US011395871B2

(12) United States Patent
Radl et al.

(10) Patent No.: US 11,395,871 B2
(45) Date of Patent: Jul. 26, 2022

(54) EXTERNAL FEMALE CATHETER SYSTEM WITH INTEGRATED SUCTION REGULATOR

(71) Applicant: Boehringer Technologies, LP, Phoenixville, PA (US)

(72) Inventors: Christopher L. Radl, Malvern, PA (US); Michael Reed Vennel, Phoenixville, PA (US)

(73) Assignee: Boehringer Technologies, LP, Phoenixville, PA (US)

( * ) Notice: Subject to any disclaimer, the term of this patent is extended or adjusted under 35 U.S.C. 154(b) by 0 days.

(21) Appl. No.: 16/996,214

(22) Filed: Aug. 18, 2020

(65) Prior Publication Data

US 2021/0113749 A1 Apr. 22, 2021

Related U.S. Application Data

(60) Provisional application No. 62/924,326, filed on Oct. 22, 2019.

(51) Int. Cl.
*A61M 1/00* (2006.01)
*A61F 5/445* (2006.01)
*A61F 5/455* (2006.01)

(52) U.S. Cl.
CPC .............. *A61M 1/743* (2021.05); *A61F 5/455* (2013.01); *A61M 1/742* (2021.05); *A61M 2202/0496* (2013.01)

(58) Field of Classification Search
CPC .... A61F 5/455; A61F 2013/4506; A61F 5/44; A61F 5/453; A61F 2002/047;
(Continued)

(56) References Cited

U.S. PATENT DOCUMENTS 4,465,481 A * 8/1984 Blake .................... A61M 27/00
604/541
4,610,675 A 9/1986 Triunfol
(Continued)

FOREIGN PATENT DOCUMENTS

WO WO-2014085099 A1 * 6/2014 ....... A61B 17/07207

OTHER PUBLICATIONS https://www.crbard.com/Medical/en-US/Products/PUREWICK-Female-External-Catheter, undated, 1 page.
(Continued)

*Primary Examiner* — Quang D Thanh
*Assistant Examiner* — Brandon W. Levy
(74) *Attorney, Agent, or Firm* — Caesar Rivise, PC

(57) ABSTRACT

A system and method for automatically removing by suction urine voided by a female. The system includes an integrated external catheter and suction regulator unit. The external catheter is applied at the female's urethra opening to receive urine voided by the female. The suction regulator is connected to a receptacle for collecting the urine and is operative to regulate suction applied to the canister from a hospitals' suction line to a regulated value which is applied the external female catheter, whereupon urine from the external female catheter is carried by the regulated suction through the suction regulator and into the receptacle. The external catheter includes an internal suction tube and an external removable and replaceable liquid permeable cover located on the internal suction tube. The external catheter is malleable so that it can be conformed to the anatomy of the female.

18 Claims, 8 Drawing Sheets

(58) Field of Classification Search
CPC .......... A61M 2202/0496; A61M 1/742; A61M 1/741; A61M 1/00; A61M 27/00; A61M 1/743; A61M 1/7415; A61M 1/74; A61M 1/90; A61M 1/84; A61M 25/0017; A61M 25/007; A61M 1/964; A61M 25/0021; A61M 25/09; A61M 3/0279
See application file for complete search history.

(56) References Cited

U.S. PATENT DOCUMENTS

| | | | |
|---|---|---|---|
| 4,747,166 A | 5/1988 | Kuntz | |
| 5,073,172 A | 12/1991 | Fell | |
| 5,678,564 A | 10/1997 | Lawrence et al. | |
| 5,894,608 A | 4/1999 | Birbara | |
| 6,024,120 A * | 2/2000 | Yam | F16K 24/06 137/495 |
| 6,849,065 B2 | 2/2005 | Schmidt et al. | |
| 7,018,366 B2 | 3/2006 | Easter | |
| 7,220,250 B2 | 5/2007 | Suzuki et al. | |
| 8,287,508 B1 | 10/2012 | Sanchez | |
| 10,646,625 B2 | 5/2020 | Radl et al. | |
| 2004/0006311 A1* | 1/2004 | Shchervinsky | A61M 1/84 604/164.01 |
| 2005/0192548 A1* | 9/2005 | Dolliver | A61M 1/3698 604/317 |
| 2007/0010798 A1 | 1/2007 | Stoller et al. | |
| 2012/0238972 A1* | 9/2012 | Karpowicz | A61M 1/74 604/319 |
| 2016/0310711 A1 | 10/2016 | Luxon et al. | |
| 2017/0266031 A1* | 9/2017 | Sanchez | A61F 5/4404 |

OTHER PUBLICATIONS https://www.ohmedical.com/External-Catheters/DRYDOCtrade-VACUUM-STATION-DD15/, 2020, 2 pages.
https://sageproducts.com/primafit-external-urine-management-system-for-females/, 2020, 3 pages.

* cited by examiner

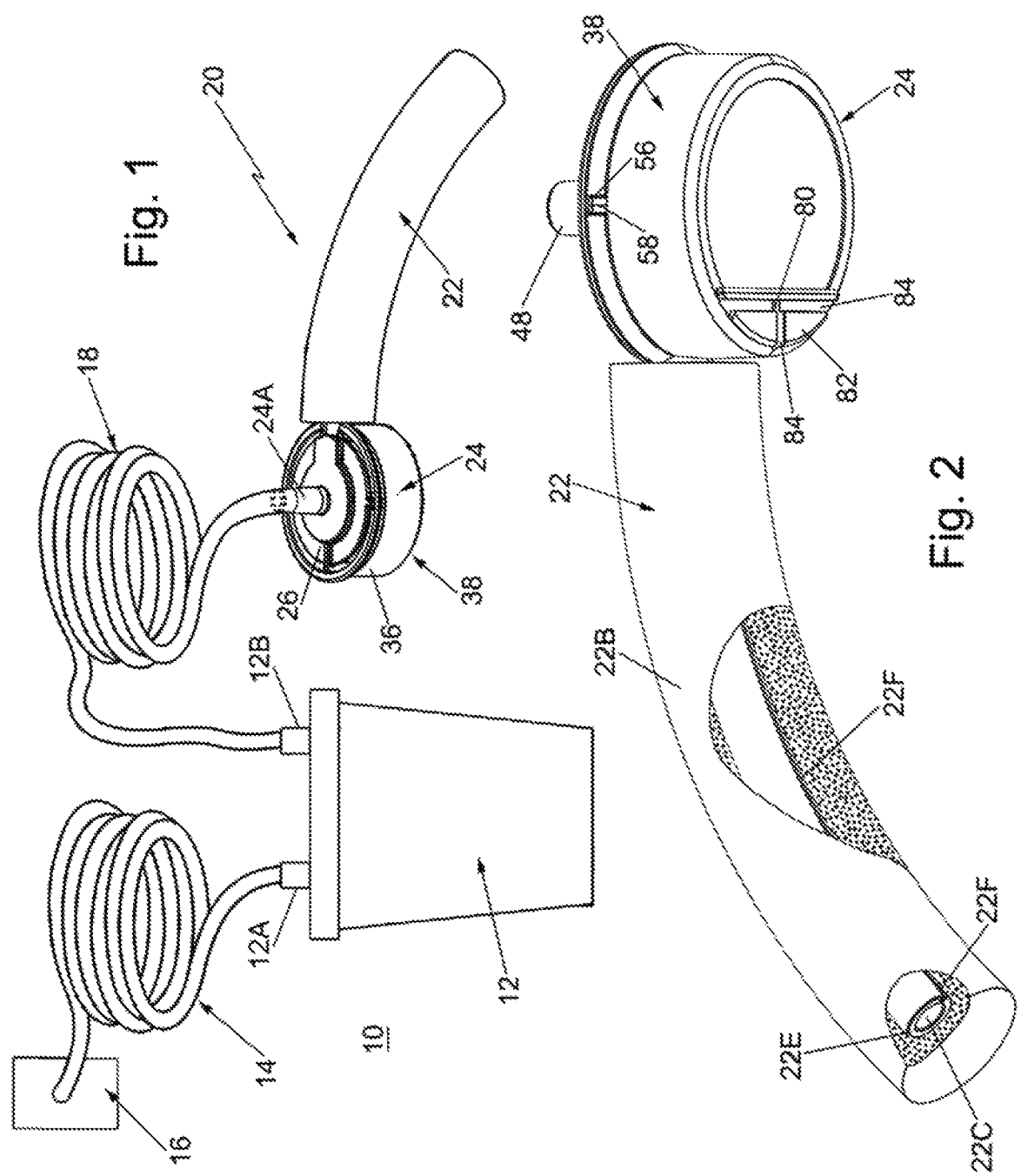

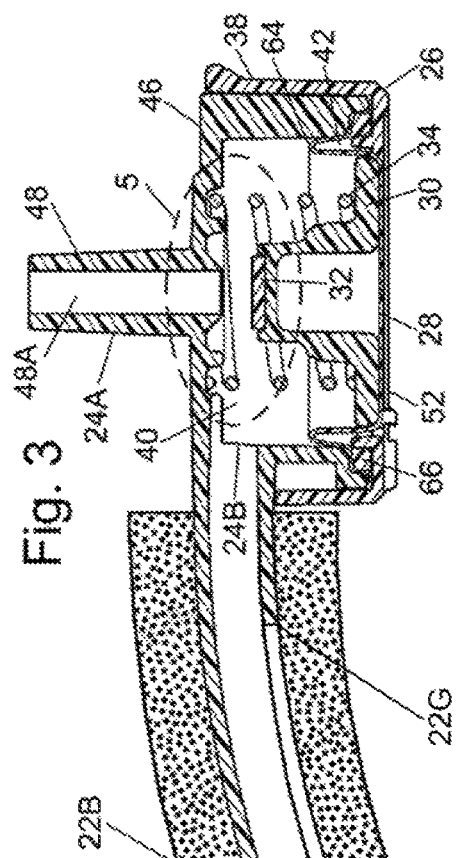
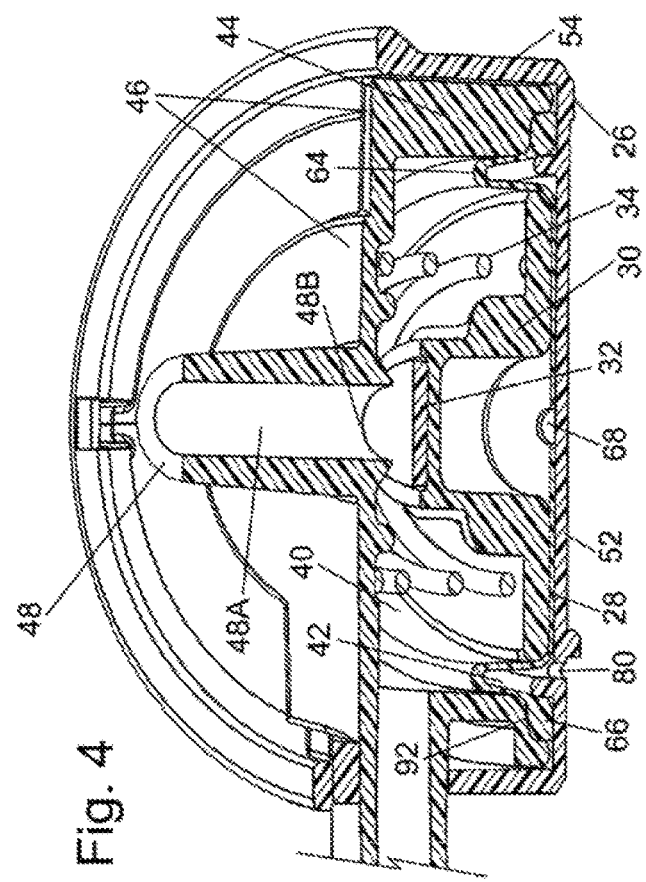
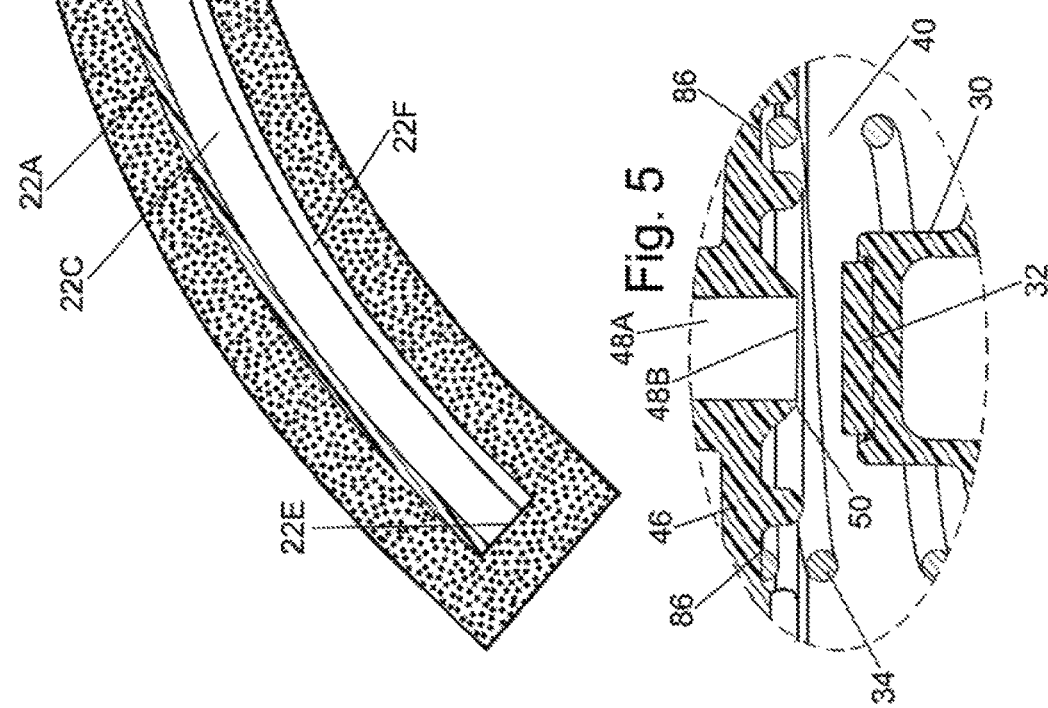

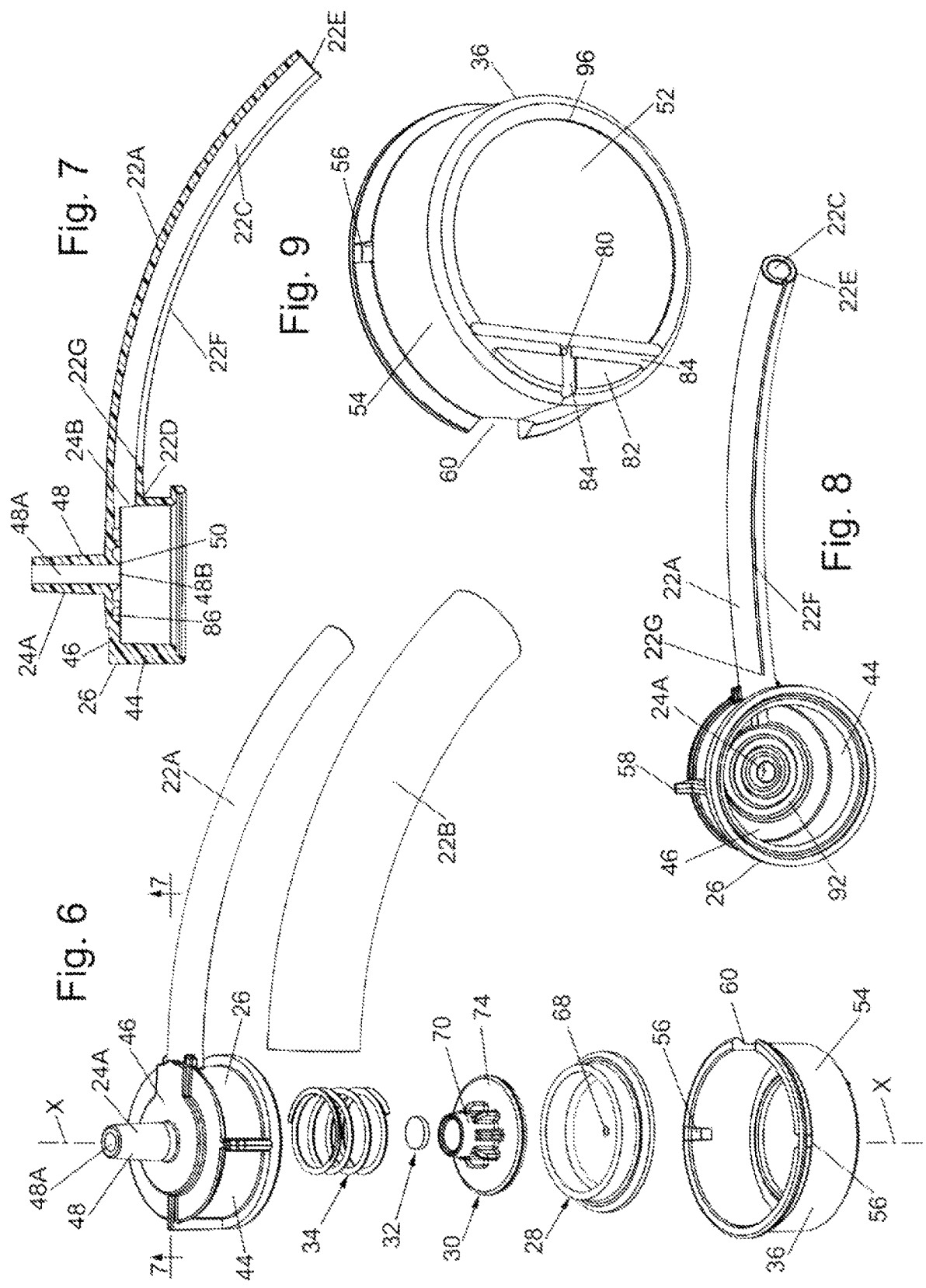

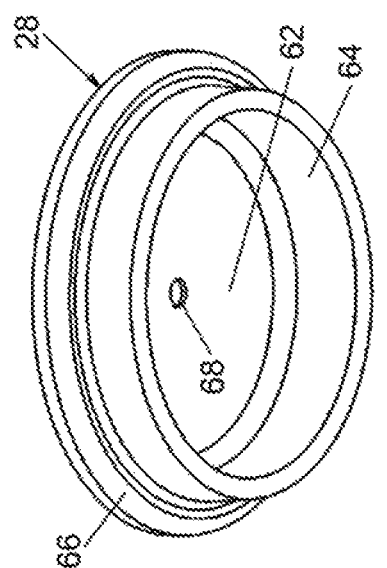
Fig. 12
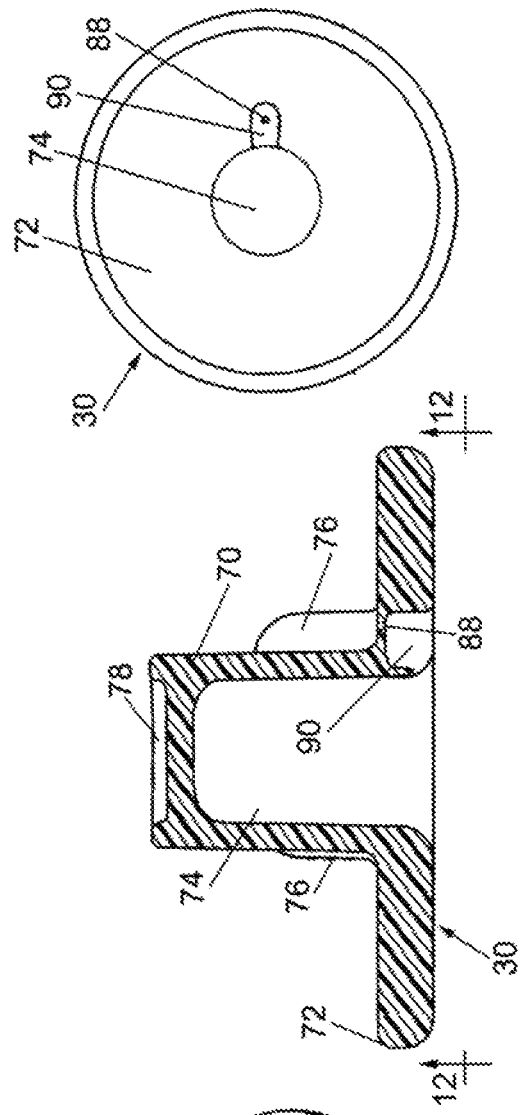
Fig. 11
Fig. 10
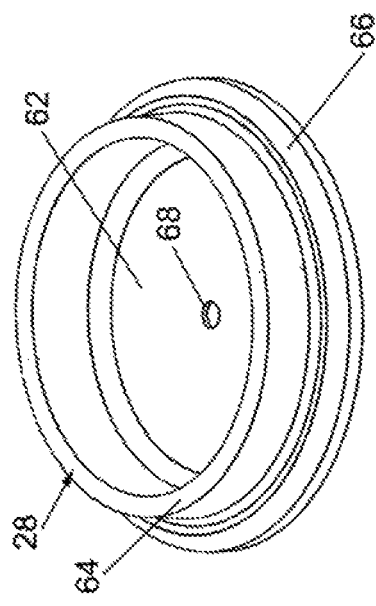
Fig. 15
Fig. 14
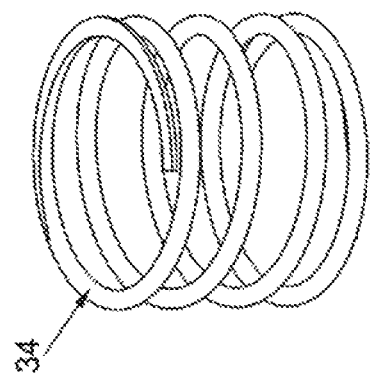
Fig. 13

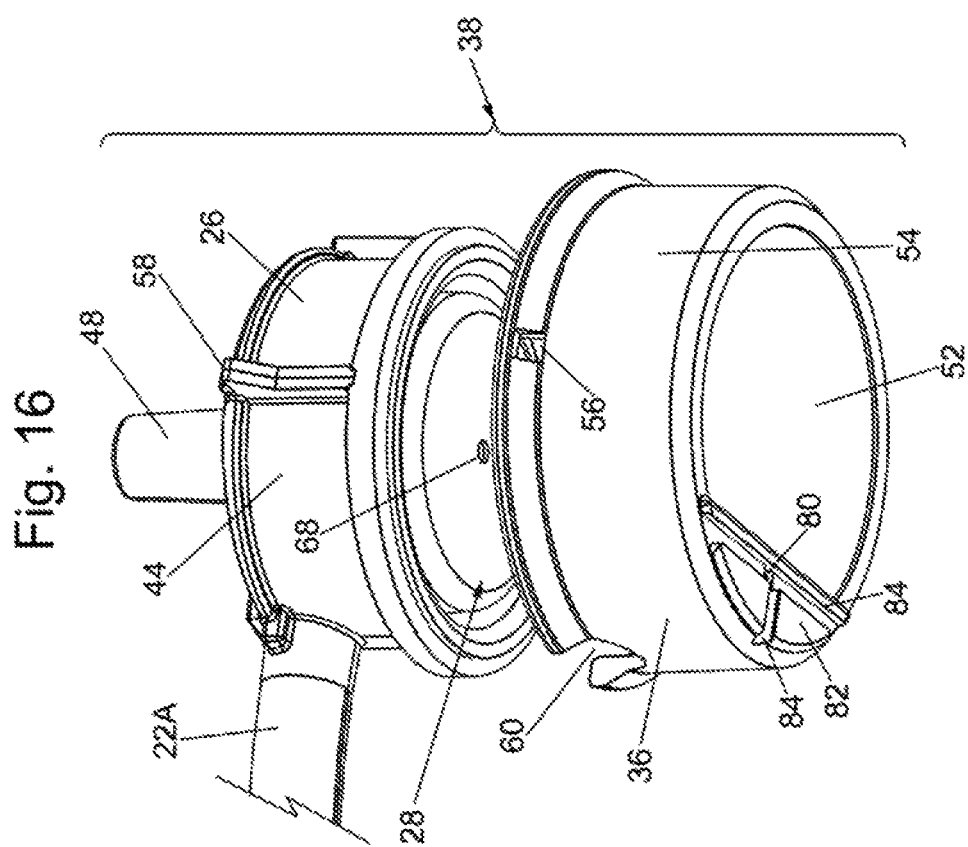

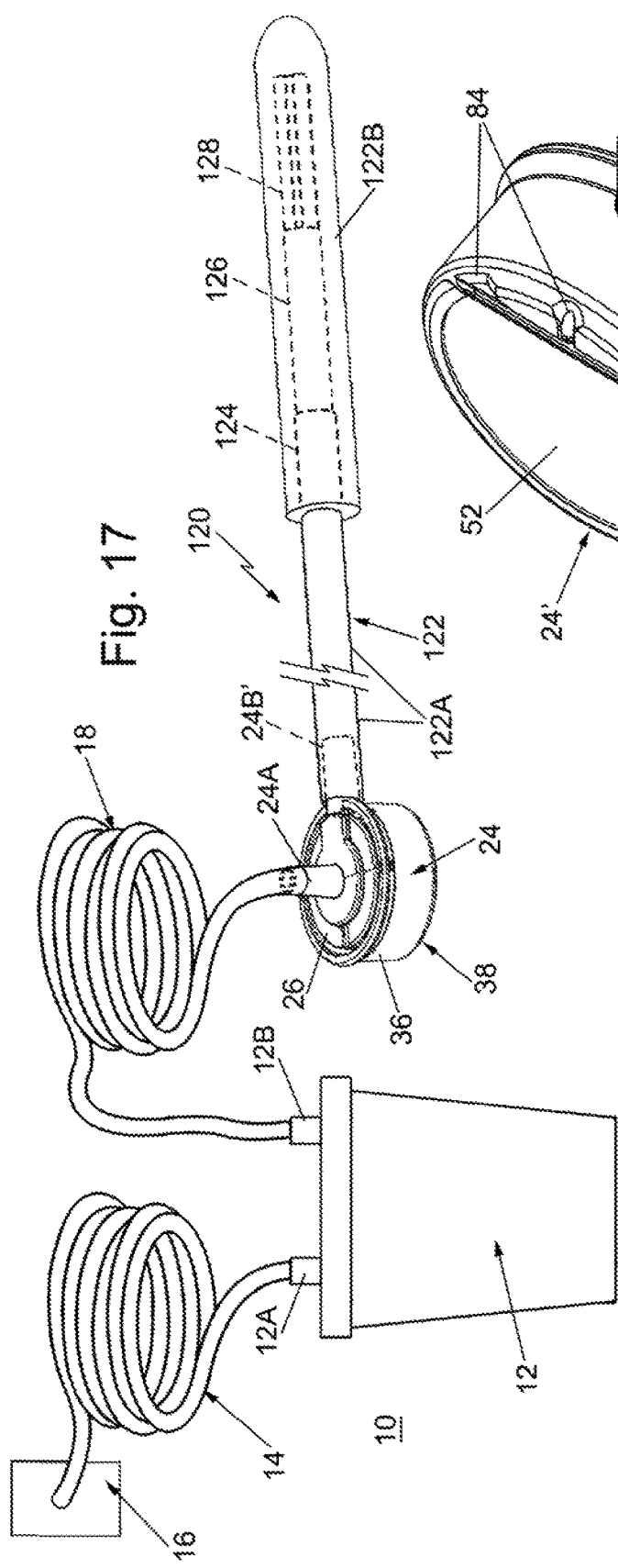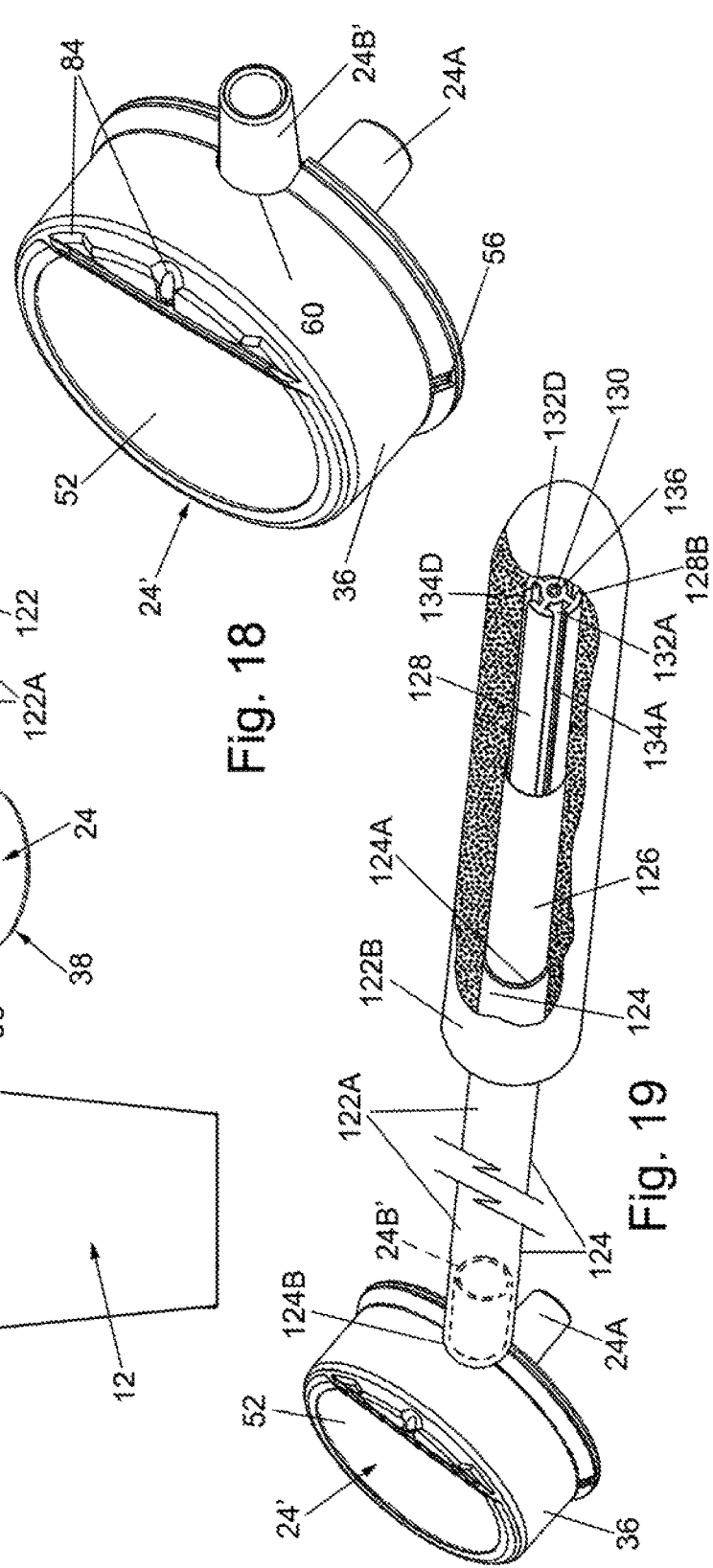

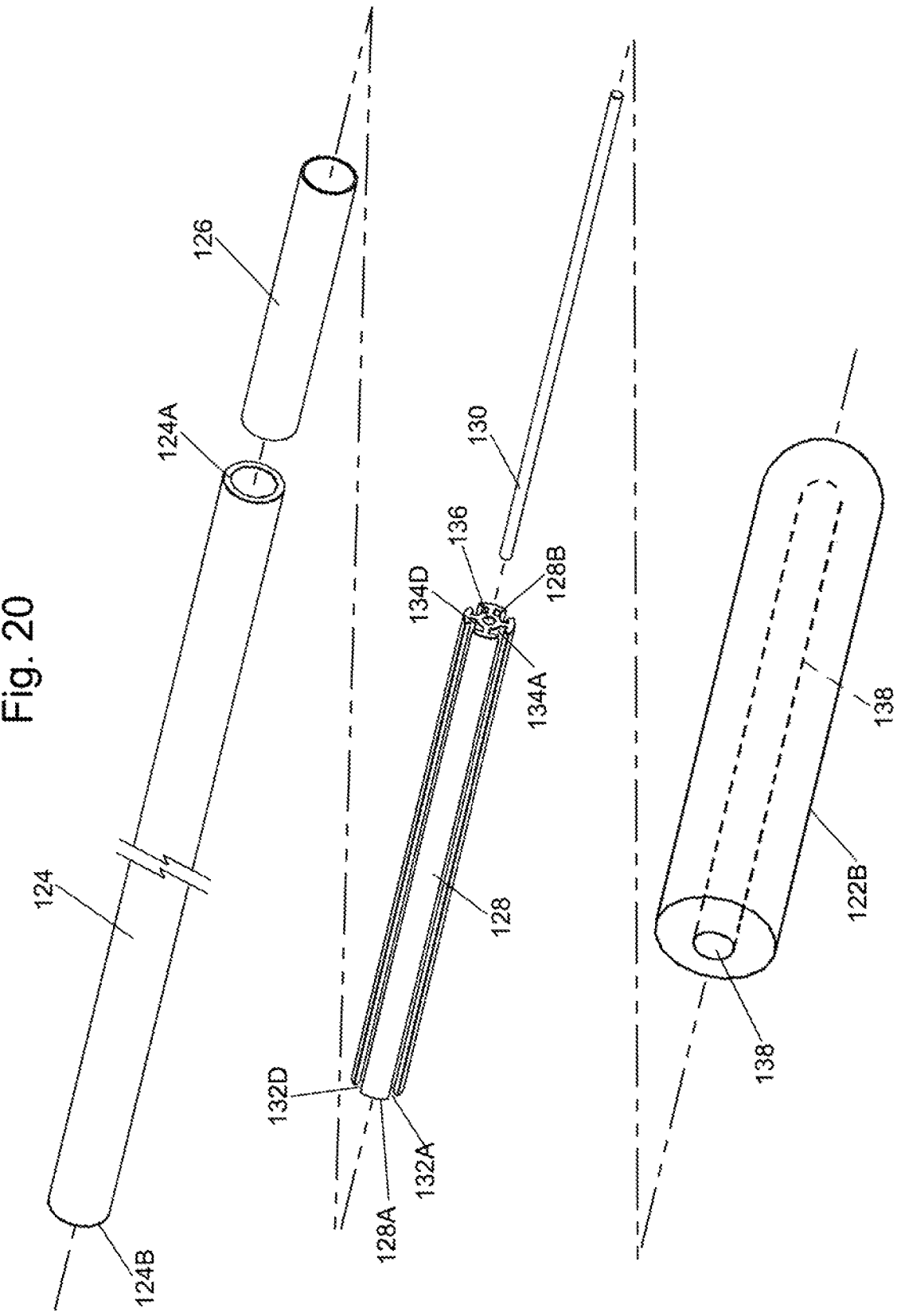

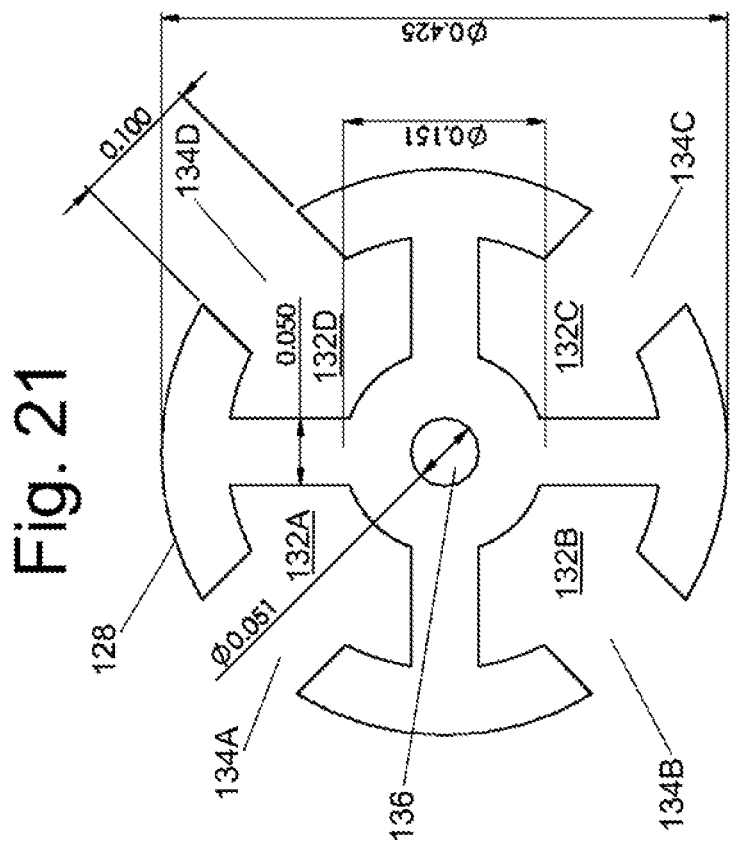

EXTERNAL FEMALE CATHETER SYSTEM WITH INTEGRATED SUCTION REGULATOR

CROSS-REFERENCE TO RELATED APPLICATIONS

This utility application claims the benefit under 35 U.S.C. § 119(e) of Provisional Application Ser. No. 62/924,326, filed on Oct. 22, 2019, entitled "External Female Catheter System With Integrated Suction Regulator And Method Of Use", the entire disclosure of which is incorporated by reference herein.

FIELD OF THE INVENTION

This invention relates generally to medical devices and methods and more particularly to devices and methods for automatically removing urine from a female patient using suction applied to an external catheter.

BACKGROUND OF THE INVENTION

Various external catheters are available for non-invasive urine output management in female patients. The PUREWICK® female external catheter available from C.R. Bard, Inc. is an example of one such device. That external catheter is a soft member having a hollow flexible body including a side opening exposing soft absorbent gauze. The catheter is configured to be positioned so that soft gauze is disposed between the patient's separated gluteus and labia and in fluid communication with the urethral opening of the patient, whereupon urine voided by the patient is wicked into the gauze. The catheter is arranged to be attached via suction tubing to a suction canister, which should in turn be connected to either a suction regulator on a hospital wall or a portable suction pump, such as the DRYDOC™ vacuum suction station of C.R. Bard, Inc., whereupon the urine wicked into the external catheter is carried by the suction into the canister for collection. The Instructions for Use (IFU) of the PUREWICK® female external catheter indicates that the suction source should be set to a minimum of 40 mmHG continuous suction.

Sage Products, LLC, now a Stryker Corporation company, provides an external urine management system for females under the trademark PRIMAFIT. That system is in many respects similar to the PUREWICK® system. In particular, the PRIMAFIT system basically comprises an external catheter body having an end cap to fit in the woman's perineal area to secure the catheter in place. The catheter includes soft wicking fabric that absorbs and diverts urine away from the patient's skin. Urine is then absorbed into the system's core and suctioned into a collection canister.

The patent literature includes various systems and methods for collecting and transporting urine away from a person's body, such as: U.S. Pat. No. 4,610,675 (Triunfol); U.S. Pat. No. 4,747,166 (Kuntz); U.S. Pat. No. 5,678,564 (Lawrence et al.); U.S. Pat. No. 5,894,608 (Birbara); U.S. Pat. No. 6,849,065 (Schmidt et al.); U.S. Pat. No. 7,018,366 (Easter); U.S. Pat. No. 7,220,250 (Suzuki et al.); and U.S. Pat. No. 8,287,508 (Sanchez).

As will be appreciated by those skilled in the art, most hospital suction regulators provide insufficient flow at low vacuum pressures, like the 40 mmHg recommended for use with the PUREWICK® female external catheter. Therefore nurses or other care givers frequently increase the vacuum to get adequate urine flow. However, the use of higher vacuum pressure poses an increased risk to the patient, as the only opening in the circuit for air to relieve the pressure is adjacent the patient's genitalia. Accordingly, use of increased vacuum pressure to increase the flow rate of urine being withdrawn into the canister runs the risk of injury to the delicate tissue adjacent the urethral opening.

In our U.S. Provisional Patent Application Ser. No. 62/829,731, filed on Apr. 5, 2019, entitled System Including Suction Regulator For Automatically Removing Urine From A Female Patient And Method Of Use Of The System, which is assigned to the same assignee as this invention, there is disclosed and claimed a disposable suction regulator configured for use between the female external catheter and a canister coupled to a source of higher suction, e.g., a regulator at the hospital's suction line. That external catheter suction regulator is designed in such a way that it allows far greater flow at low pressures than do the traditional wall regulators. As such, it provides an efficient means for removing urine from a patient using an external catheter, wherein the flow rate is sufficiently high for increased effectiveness, yet is produced by a suction level that is sufficiently low to minimize the danger of injury to the delicate tissue of the patient adjacent the patient's urethral opening.

All of the references as cited herein are specifically incorporated by reference The subject invention improves upon the invention of our aforementioned earlier filed provisional application by providing an external female catheter and a suction regulator in an integral unit, which is simple in construction, low in cost, comfortable to use, and effective and safe in operation.

SUMMARY OF THE INVENTION

One aspect of this invention is an integrated unit for automatically removing by suction urine voided by a female and providing that urine to a receptacle or canister coupled to a source of suction providing suction having a first value. The integrated unit comprises an external catheter and a suction regulator. The external catheter configured for external disposition in fluid communication with a urethra opening of the female whereupon urine voided by the female is received by the external catheter. The external catheter comprises an elongated suction tube and a removable cover. The elongated suction tube comprises a first section and a second section. The first section has a distal end, a proximal end, at least one longitudinal passageway extending through the first section from the distal end to the proximal end, and at least one continuous elongated slot extending along the at least one passageway from the distal end to a point adjacent the proximal end. The at least one continuous elongated slot is in fluid communication with the at least one longitudinal passageway. The second section is located proximally of the first section and comprises a passageway in fluid communication with the at least one longitudinal passageway. The removable cover is formed of a liquid permeable material disposed over and about the elongated suction tube to completely cover the first section. The removable cover is configured to be removed from the first section for disposal and replacement by another similarly constructed removable cover. The suction regulator comprises a housing including a first portion to which the second section is secured and a second portion forming a suction port. The suction port is configured to be coupled to the receptacle or canister, whereupon the suction regulator is interposed between the external catheter and the receptacle or canister to regulate the amount of suction from the first value to a regulated value lower than the first value and to apply regulated suction at the regulated value to the external catheter, whereupon urine from the external catheter is carried through the suction regulator and into the receptacle or canister.

In accordance with one preferred aspect of the integrated unit of this invention, the distal end of the first section is open.

In accordance with another preferred aspect of the integrated unit of this invention, the first section is malleable In accordance with another preferred aspect of the integrated unit of this invention, the first section comprises at least three equidistantly spaced longitudinal passageways and at least three continuous elongated slots extending along the at least three equidistantly spaced longitudinal passageways.

In accordance with another preferred aspect of the integrated unit of this invention, the first section includes a central passageway surrounded by the at least three equidistantly spaced longitudinal passageways and a malleable wire extending through the central passageway.

In accordance with another preferred aspect of the integrated unit of this invention, the removable cover comprises a sponge material.

In accordance with another preferred aspect of the integrated unit of this invention, the receptacle or canister comprises a first port, a second port, and a hollow interior in fluid communication with the first and second ports. The first port is configured to be connected to the source of suction, and wherein the suction regulator comprises a first port in fluid communication with the proximal end of the elongated suction tube to provide the regulated suction thereat to carry urine from the external catheter through the suction regulator and through the suction port into the second port of the receptacle or canister for collection in the hollow interior of the receptacle or canister.

In accordance with another preferred aspect of the integrated unit of this invention the regulated value of suction is within the range of approximately 40-60 mmHg.

In accordance with another preferred aspect of the integrated unit of this invention the urine is carried through the suction regulator into the receptacle or canister by air, which is flowing at a flow rate up to approximately 100 standard cubic feet per hour.

In accordance with another preferred aspect of the integrated unit of this invention the suction regulator comprises a first chamber, a second chamber, a movable diaphragm and a biasing member. The first chamber is configured to have suction applied thereto from the receptacle or canister. The second chamber is at atmospheric pressure. The movable diaphragm separates the first chamber from the second chamber, whereupon a differential pressure exists between the first and second chambers. The differential pressure imparts a differential pressure force on the movable diaphragm. The biasing member is configured to impart a counter force on the movable diaphragm that opposes the differential pressure force.

In accordance with another preferred aspect of the integrated unit of this invention the first chamber comprises a valve seat and a movable sealing member coupled to the movable diaphragm. The valve seat surrounds an opening for fluids within the first chamber to flow therethrough. The sealing member blocks the opening when the differential pressure force exceeds the counter force imparted by the biasing member.

In accordance with another preferred aspect of the integrated unit of this invention the suction regulator comprises a bleed hole in the moveable diaphragm to enable ambient air from the second chamber to enter into the first chamber.

In accordance with another preferred aspect of the integrated unit of this invention the first and second chambers are located within a housing assembly, and wherein the second chamber includes a bleed hole in the housing assembly in communication with the ambient atmosphere.

In accordance with another preferred aspect of the integrated unit of this invention the bleed hole in the housing assembly is located within a recess having at least one opening at an end thereof to prevent blockage of the bleed hole.

Another aspect of this invention is a method for automatically removing urine from a female patient. The method comprises providing a receptacle or canister for collecting urine, providing an integrated unit including an external catheter and a suction regulator, whereupon the external catheter is in fluid communication with a urethra opening of the female such that urine voided by a female patient is received by the external catheter. The receptacle or canister is coupled to a source of suction providing suction having a first value. The suction regulator automatically regulates the amount of suction from the first value to a regulated value lower than the first value and applies the regulated suction at the regulated value to the external catheter to carry urine from the external catheter through the suction regulator and into the receptacle or canister.

In accordance with one preferred aspect of the method of this invention the regulated value of suction is within the range of approximately 40-60 mmHg.

In accordance with another preferred aspect of the method of this invention the urine is carried through the suction regulator into the receptacle by air which is flowing at a flow rate up to approximately 100 standard cubic feet per hour.

DESCRIPTION OF THE DRAWING

FIG. 1 is an illustration of one exemplary system for automatically removing urine from a female patient making use of an integrated unit having an external female catheter and suction regulator constructed in accordance with this invention and which can be used in a method of this invention;

FIG. 2 is an enlarged isometric view, partially in section, of the integrated external female catheter and suction regulator unit shown in FIG. 1;

FIG. 3 is an enlarged longitudinal sectional view of the integrated external female catheter and suction regulator unit shown in FIG. 2;

FIG. 4 is an enlarged sectional view of the suction regulator portion of the integrated external female catheter and suction regulator unit shown in FIGS. 2 and 3;

FIG. 5 is an enlarged sectional view of the portion of the suction regulator shown within the area designated by the broken line oval designated by the reference number 5 in FIG. 3;

FIG. 6 is an exploded isometric view of the various components making up the integrated external female catheter and suction regulator unit shown in FIGS. 2 and 3;

FIG. 7 is a reduced size longitudinal sectional view of one component, i.e., a body portion and an integrated suction tube, forming a portion of the integrated external female catheter and suction regulator unit shown in FIGS. 2 and 3;

FIG. 8 is a reduced size isometric view of the component of the integrated external female catheter and suction regulator unit shown in FIG. 7;

FIG. 9 is an enlarged isometric view of another component, i.e., a cap member, of the integrated external female catheter and suction regulator unit shown in FIGS. 2 and 3;

FIG. 10 is an enlarged isometric view of another component, i.e., a piston, of the integrated external female catheter and suction regulator unit shown in FIGS. 2 and 3;

FIG. 11 is a sectional view taken along line 11-11 of FIG. 10;

FIG. 12 is a reduced plan view taken along line 12-12 of FIG. 11;

FIG. 13 is an enlarged isometric view of another component, i.e., a biasing spring, of the integrated external female catheter and suction regulator unit shown in FIGS. 2 and 3;

FIG. 14 is an enlarged isometric view of another component, i.e., a diaphragm, of the integrated external catheter and suction regulator unit shown in FIGS. 2 and 3;

FIG. 15 is an enlarged isometric view of the diaphragm of FIG. 14 but taken from a different angle;

FIG. 16 is an enlarged isometric view showing the assembly of the cap member of FIG. 9 to the body portion and integrated suction tube component of FIGS. 7 and 8 to complete the assembly of the integrated external female catheter and suction regulator unit shown in FIGS. 2 and 3;

FIG. 17 is an illustration, similar to FIG. 1, but showing another exemplary system for automatically removing urine from a female patient making use of a more preferred integrated unit having an external female catheter and suction regulator constructed in accordance with this invention and which can be used in a method of this invention;

FIG. 18 is an isometric view of an alternative suction regulator forming a portion of the more preferred integrated unit shown in FIG. 17;

FIG. 19 is an enlarged isometric view, partially in section, of the integrated external female catheter and suction regulator unit shown in FIG. 17;

FIG. 20 is an enlarged exploded isometric view of another portion of the integrated external female catheter and suction regulator unit shown in FIG. 17; and FIG. 21 is a greatly enlarged end view of one of the components, i.e., a multi-slot end-piece, making up a portion of the integrated external female catheter and suction regulator unit shown in FIG. 17.

DETAILED DESCRIPTION OF THE PREFERRED EMBODIMENT

Referring now to the various figures of the drawing wherein like reference characters refer to like parts, there is shown in FIG. 1 one exemplary embodiment of a system 10 including an integrated external female catheter and suction regulator unit 20 constructed in accordance with one exemplary preferred embodiment of this invention for automatically removing urine from a female patient.

The details of the integrated external female catheter and suction regulator unit 20 will be described later. Suffice it for now to state that the unit 20 basically comprises an external catheter 22 and a suction regulator 24 which when assembled together form an integrated (one-piece) unit. The external catheter 22 portion of the unit 20 basically comprises a suction tube 22A and a removable liquid permeable cover 22B. The cover 22B is disposed over and surrounding the suction tube 22A. When the unit 20 is in use the cover 22B placed against the urethra opening of a female patient to serve as a urine wicking member to receive urine which has been excreted by the patient. The suction regulator 24 portion of the unit 20 serves to provide a suitable safe regulated level of suction to the external catheter to effectively draw urine from the cover 22B through a longitudinally extending slot (to be described later) in the suction tube 22A into and through the suction regulator 24 to deliver it to a receptacle or canister 12, which forms a portion of the system 10.

The receptacle or canister 12 is of conventional construction and includes a port 12A that is configured to be connected, via a section of conventional tubing 14, to a suction source, e.g., a wall regulator 16 of the hospital's main suction line which provides suction to the suction regulator 24. The wall regulator 16 should be set to line vacuum or the maximum available vacuum pressure if a line function is not available. The canister 12 includes another port 12B, which is connected, via another section of conventional tubing 18, to a "line suction port" 24A, of the suction regulator 24. The suction regulator 24 includes another port, which is internal and hereinafter identified as the "regulated suction port" 24B, which is connected to and in fluid communication with the proximal end of a suction tube 22A.

As will also be described later the suction regulator 24 is configured to enable flow through it from the external catheter to the canister nearing the maximum the hospital's suction line or regulator 16 is capable of sustaining without allowing the pressure to rise above a desired operating value, e.g., 40 mmHg, of the suction regulator 24 in the event the external catheter becomes sealed against the patient. Since the suction regulator 24 is located between the external catheter 22 and the urine collecting canister or receptacle 12, the regulator 24 will be closer to the catheter 22 than if it was located between the canister or receptacle 12 and the hospital suction line or regulator 16, thereby enabling the maximum possible urine flow, but necessitates the urine flowing through the regulator. To that end, the entire unit 20 is intended to be a non-sterile, single-patient-use disposable unit.

Turning now to FIGS. 2, 3, 7 and 8, the details of the external catheter portion 22 will now be described. As mentioned above it basically comprises the suction tube 22A and the liquid permeable cover 22B. The suction tube 22A is an elongated arcuate member having a central passageway 22C extending the length thereof from its proximal end 22D to its distal end 22E. The distal end 22E is open. The proximal end 22D is also open and forms the heretofore identified internal port 24B (FIG. 3) of the suction regulator. The proximal end of the suction tube is secured to a portion of a housing assembly (to be described later) of the suction regulator. That portion of the housing assembly constitutes a hollow housing body 26. As best seen in FIGS. 7 and 8, the suction tube 22A includes a longitudinally extending slot 22F extending approximately the entire length thereof from a point 22G adjacent the housing body 26 to the distal end 22E. The slot is in fluid communication with the central passageway 22C of the suction tube 22 along the entire length of the slot. The portion of the suction tube 22A that includes the slot 22F constitutes a first or distal section of the suction tube, and the portion of the suction tube that is connected to the portion of the housing assembly constitutes a second or proximal section of the suction tube.

The cover 22B is a cylindrical member formed of a liquid permeable material, preferably one that is absorbent and hydrophilic, e.g., a polyurethane or a PVA (polyvinyl alcohol) sponge, although it could be formed of other liquid permeable materials such as, cellulose, polyurethane, gauze, etc. As best seen in FIG. 2 the cover 22B includes a central passageway extending from its proximal end to a point adjacent its distal end. The internal diameter of the central passageway of the cover 22B is approximately the same size or slightly smaller than the external diameter of the suction tube 22A so that the suction tube can be located therein, with the cover held thereon by friction, whereupon the closed distal end of the cover closes the open distal end 22E of the suction tube. Moreover, the cover extends the entire length of the suction tube up to a point immediately adjacent the housing body 26. Accordingly, when regulated suction produced by the suction regulator 24 (as will be described later) is applied at the port 24B that regulated suction will appear along the length of the slot 22F to draw any urine that the female patient voided into the cover from there into the slot whereupon that urine will be pulled into the passageway 22C and carried by air from through that passageway to the suction regulator 24. From there the urine is carried to the receptacle or canister 12. In particular, with the system 10 as described above when suction is applied from the hospital's suction line or wall regulator 16, that high level of suction is conveyed through the tubing section 14, from whence it is applied to the canister or receptacle 12 and the associated tubing section 18 to the line suction port 24A of the suction regulator 24, whereupon it is regulated (e.g., reduced) by operation of the suction regulator to a much lower operating level, e.g., 40 mmHg. That reduced or regulated suction will appear on the suction port 24B of the regulator 24 and from there to the external catheter 22 to thereby draw urine from the external catheter 22 back through the regulator 24, and out through the tubing section 18 into the receptacle or canister 12 for collection therein.

It should be noted that for many applications the operating level is preferably approximately 40 mmHg. However, that level could be raised up to approximately 60 mmHg, since some hospitals are comfortable with higher vacuum pressures. If desired the system 10 may also include an overflow detector of any suitable construction to provide an indication that the amount of urine within receptacle has reached a predetermined threshold, e.g., is about to overflow, and/or to provide a signal to a controller (not shown) stop to halt the operation of the system so that no further urine is drawn into the receptacle until it can be emptied. For example, the canister 12 may include a shut off float valve and/or a filter at outlet 12A to prevent possible contamination of the hospital's main suction.

As should be appreciated by those skilled in the art from the discussion to follow the operation of the suction regulator 24 ensures that a desired level of suction is applied to the external catheter 22 to ensure proper and safe operation of the system, i.e., to maximize the rate at which urine may be withdrawn from the catheter into the receptacle or canister without subjecting the delicate tissue of the woman at her urethra opening to injury, e.g., a hematoma, from excess suction thereat.

Turning now to FIGS. 3-6, the construction of the suction regulator portion 24 of the unit 20 will now be described. To that end as can be seen the suction regulator 24 basically comprises a flexible diaphragm 28, a piston 30, a sealing disk 32, a helical compression spring 34, and a housing assembly 38. The housing assembly 38 is made up of the heretofore identified housing body 26 and a lid or cover 36. The lid or cover 36 and the housing body 26 are configured to be connected together, as will be described later and as shown in FIG. 16, to form the hollow housing assembly 38. That assembly encloses (houses) the other components making up the suction regulator 24. The housing body 26 and the cover 36 are preferably formed of a rigid plastic, such as ABS, although other plastics can be used. The suction tube 22A, being integral with the housing body 26 is also formed of the same material as the housing body, but could be formed of some other material. That other material may be chosen to exhibit some degree of flexibility to enhance engagement of the external catheter 22 with the portion of the female's body contiguous with her urethra opening As best seen in FIGS. 3-8 the housing assembly 38 defines two internal chambers, namely, an upper chamber 40 and a lower chamber 42, which are separated from each other by a portion of the diaphragm 28. The housing body 26 includes a circular annular sidewall 44 projecting downward from a top wall 46. The circular sidewall 44 extends about a central axis X (FIG. 6) of the suction regulator. A tubular extension 48 extends upward from the top wall and centered on the axis X. The tubular extension forms the heretofore identified line suction port 24A and includes a passageway 48A extending through it. The lower end of the passageway 48A is open at 44B, with the portion of the top wall 46 contiguous with the opening 48B forming a beveled or conical surface valve seat 50 (FIG. 5). The opening 44B is in fluid communication with the upper chamber 40 in the interior of the housing assembly 38 of the suction regulator 24. The upper or free end of the passageway 48A is open and configured so that the distal end of the tubing section 18 can be connected to it, whereupon the passageway extending through that tubing section will be in fluid communication with interior of the housing assembly 38 and with upper chamber 40.

The lid or cover 36 is a generally cup-shaped member having a generally planar bottom wall 52 and a circular annular sidewall 54 projecting upward therefrom. The sidewall 54 includes a pair of diametrically opposed notches 56 immediately adjacent the lower edge of the sidewall. As can be seen in FIG. 16 the notches 56 are configured to receive respective diametrically opposed projecting tabs 58 of the housing body 26 to secure the lid or cover 36 to the housing body 26 and thus complete the housing assembly 38. The sidewall 54 of the lid or cover 36 also includes an arcuate recess 60 (FIG. 9) in the edge of the sidewall located midway between the notches 56. The recess 60 serves to receive the suction tube 22A when the lid or cover 36 is secured to the housing body 26.

The diaphragm 28 is best seen in FIGS. 14 and 15, and is preferably a rolling diaphragm formed of any resilient flexible material, e.g., silicone, nitrile, etc. The diaphragm includes a generally planar circular central portion 62 and a folded generally V-shaped or U-shaped edge portion 64 surrounding the central portion and terminating in a flanged generally planar thickened periphery 66. A small opening or hole 68 is located in the center of the central portion 62. The central portion 62 is disposed on a planar top surface of the piston 30 (to be described later), with the thickened periphery 66 of the diaphragm disposed on an annular ledge 92 (FIG. 4) at the lower end of the sidewall 44 of the housing body 26 between that ledge and the inner surface of the bottom wall of the lid or cover 36. With the lid or cover secured to the housing base 26 the thickened periphery 66 of the diaphragm 28 is tightly sandwiched between the ledge and the inner surface of the lid or cover. This arrangement divides the interior of the suction regulator into the heretofore identified upper chamber 40 and lower chamber 42. In particular, the upper chamber is formed between the inner surface of the top wall 46 of the body member 26, the contiguous inner surface of the sidewall 44 of the body member, the upper surface of a portion of the diaphragm 28 and a portion of the piston 30. The lower chamber 42 is formed between the inner surface of bottom wall 52 of the lid or cover 36, and the central portion 62 and contiguous V or U-shaped portion 64 of the diaphragm 28.

The piston 30 is best seen in FIGS. 10 and 11 and basically comprises a unitary body formed of a rigid plastic, such as ABS. The body includes a central hub 70 whose bottom end terminates in a circular flange 72. The bottom surface of the flange is planar, but includes a circular recess 74 in the center thereof and extending into the hub 70. A plurality of ribs 76 extend outward radially from the hub and serve to reinforce the flange 72 and to center the biasing spring 34 about the central axis X. The top surface of the hub 70 includes a recess 78 for receipt of the sealing disk 32.

The sealing disk 32 is fixedly secured in the recess 78 of the piston 30 and serves as a valve member to engage the valve seat 50 in the upper chamber 40 when excess suction is applied (as will be described later). The sealing disk 32 is formed of any suitable material, e.g., silicone rubber.

The cover or lid 36 includes a small opening or vent (FIGS. 2, 4, 9 and 15) to the ambient atmosphere which will be referred to as the "atmospheric reference port" 80. The atmospheric reference port ensures that the lower chamber 42 will be at the pressure of the ambient atmosphere. In particular, the port 80 extends through the thickness of the cover and is in fluid communication with the interior of lower chamber 42 to maintain that chamber at atmospheric pressure. Inasmuch as the atmospheric reference port 80 is located in the bottom surface of the cover 36, it is susceptible to being blocked or covered by a sticker, some other object or even a portion of the female's body. To prevent such an occurrence the lid or cover is shaped to prevent blockage of the port 80. In particular, the lid or cover includes a thickened portion 82 located adjacent the port 80 with an elongated shallow tripartite or T-shaped recess or slot 84 extending into the thickened portion. The outer edge of the atmospheric reference port 80 is located at the bottom of the slot 84 at the intersection of the slot's various three sections and is in fluid communication with each of those sections. The outer end of each of the slot sections is open. Thus, if something should be on the surface of the thickened portion 82 of the lid or cover disposed over the atmospheric reference port 80 air can still enter into that port via any open end of the T-shaped slot 84.

A label (not shown) bearing indicia or information regarding the unit 20 may be fixedly secured within a very shallow recess 96 in the outer surface of the lid or cover adjacent the thickened portion 82 so its presence does not block the T-shaped slot 84.

The biasing spring 34 is a helical compression spring formed of any suitable material, e.g., stainless steel. As best seen in FIGS. 3-6 and 13, the spring is located within the upper chamber 40, with the lower end of the spring in engagement with the undersurface of the flanged portion 72 of the piston 30 and surrounding a piston's central hub 70 and with the upper end of the spring located within an annular recess 86 (FIG. 5) in the undersurface of the top wall 46 of the housing body 26. The spring is under compression to bias the piston and diaphragm downward and away from the valve seat 50.

As mentioned above, the suction regulator 24 regulates the level of suction to a desired operating value, e.g., 40 mmHg, and provides the regulated suction to the external catheter (the urine wicking member) 22. To that end, the regulator 24 is configured to limit the amount of suction applied to the external catheter to that desired value even if a level of suction greater than that predetermined value is applied to the suction regulator from the suction source (particularly if the suction source is at a much higher level, which will typically be the case if the suction source is the hospital's suction line). The predetermined or desired suction value (hereinafter referred to has the "regulator's set-point" or "regulated set-point value") is fixed and is factory-established by the spring 34 and dimensions of the housing body 26, the cover or lid 36, the piston 34 and the sealing disk 32. In this regard the pressure within the lower chamber 42 will be equal to atmospheric pressure by virtue of the communication of that chamber with the ambient atmosphere via the atmospheric reference port 80. With suction applied, the pressure within the upper chamber 40 will be lower than the atmospheric pressure within the lower chamber 42. The differential pressure between the chambers 40 and 42 will force the diaphragm 28 and the piston 30 upward toward the valve seat 50. The compression spring 34, however, will impart a counter force on the piston and diaphragm that opposes the differential pressure force, thereby forcing the piston upward such that the level of suction appearing at the regulated suction port 24B is the desired operating value, e.g., 40 mmHg.

If the suction applied via line suction port 24A is greater that the predetermined value or level the piston 30 and diaphragm 28 will move such that the sealing disk 32 on the piston's hub 70 comes into engagement with the valve seat 50, thereby isolating the upper chamber 40 from the suction appearing on the line suction port 24A. This action thereby limits the level of suction in upper chamber and hence at external catheter 22 to the predetermined level (operating value). If, however, the suction applied via line suction port 24A is less than the predetermined operating level the piston and diaphragm will only move part of the way downward. As such the level of suction applied to the line suction port 24A will equal that in the regulated suction port 24B and that applied to the external catheter 22.

It should be pointed out at this juncture that the suction regulator 26 is also configured to prevent the sealing disk 32 on the piston from becoming stuck for an extended period of time on the valve seat 50 in the event of what will be referred to hereinafter as an "over-travel situation". In this regard, if the suction regulator 24 is operated in a manner such that a high level of suction is applied very rapidly, the piston may experience an over-travel situation wherein it moves upward very quickly such that the sealing disk 32 becomes stuck on the valve seat 50. Under this condition the suction applied to the suction tube 24A of the external catheter would be at a higher level than the suction regulator 24 was set to provide, e.g., 40 mmHg. The suction regulator could thus stay in that state for an extended/indefinite period of time, particularly if the external catheter becomes blocked, e.g., its wicking portion (the sponge cover 24B) is in tight engagement with the vaginal tissue surrounding the urethral opening and not over the urethral opening itself. To prevent such an occurrence, the regulator 24 includes two "bleed" holes. One bleed hole is the heretofore-identified small hole 68 located in the center of the diaphragm 28. The second bleed hole is identified by the reference number 88 and is located in the piston 30. In particular, as best seen in FIG. 11, the cylindrical cavity 74 in the piston contiguous with the bottom surface of the flanged portion 72 includes a radially extending recess 90. The bleed hole 88 is located in that recess and extends through the flanged portion of the piston. Since the bleed hole 68 in the diaphragm 28 is located in the center thereof, i.e., on the central axis X, it will overlie and be in fluid communication with the cylindrical cavity 74 in the piston. The recess 90 is in fluid communication with the cylindrical cavity 74. Thus, the bleed hole 88 in the piston will be in fluid communication with the bleed hole 68 in the diaphragm. Since the bleed hole 68 in the diaphragm is in communication with the lower chamber 42, that chamber will be in fluid communication with the upper chamber 40 via the communicating bleed holes 68 and 88. Hence, if the sealing disk 32 on the piston should become stuck on the valve seat 50, air which enters into the lower chamber 42 via the atmospheric reference port 80 can then pass through the bleed hole 88 into the cylindrical cavity 74, and from there through recess 90 into the bleed hole 88, from whence it will enter into the upper chamber 40. The ingress of air into the upper chamber will decrease the vacuum within that chamber, thus enabling the spring 34 to move the piston 30 downward so that the sealing disk 32 is off of the valve seat 50.

It must be pointed out at this juncture that the sealing disk 32 becoming stuck on the valve seat 50 may not be an issue. In such a case the diaphragm 28 need not include the bleed hole 68, and the piston 30 need not include the bleed hole 88 and the associated recess 90.

In accordance with one exemplary preferred embodiment of the suction regulator 24, inner diameter of the lower chamber 42 is approximately 1.5 inch. The inner diameter of the upper chamber 40 is approximately 1.5 inch. The spring is configured to naturally apply a bias force of approximately 1.0 pound. The inner diameter of the passageway 48A is approximately 0.25 inch. The opening 48B located within the bounds of the valve seat 50 is approximately 0.22 inch. The atmospheric reference port 80 is approximately 0.035 inch in diameter. The bleed hole 88 is approximately 0.016 inch in diameter. The bleed hole 68 is approximately 0.062 inch in diameter. Each tubing section 14 and 18 is conventional having an internal passageway of approximately 0.25 inch in diameter, and each section is approximately six feet in length, but could be shorter or longer depending upon the application. In any case with an integrated external female catheter and suction regulator unit 20 sized as just described, in a system like that described during typical operation the flow rate of air into the upper chamber 40 via bleed holes should be in the range of approximately 3 to 10 standard cubic feet per hour (SCFH). In fact, benchtop testing suggests that one version of the system 20 of this invention, making use of its disposable regulator 26 is capable of air flow rates up to 100 SCFH as compared to the 15 SCFH rate observed with some commercially available wall regulator set to the suggested 40 mmHg. The additional flow allows for increased urine capture at the interface of the actual catheter, faster drying of the catheter (which helps prevent skin breakdown and infection) and pulls the urine through the tubing into the canister 30 more efficiently. This is especially true if the tubing drapes down below the height of the patient and canister.

The integrated external female catheter and suction regulator unit 20 of this invention is designed for use with a single female patient over a prolonged period of time and after use with that patient, it is to be disposed. The cover 22B is however designed to be replaced on the suction tube whenever necessary for that particular patient. To replace the cover 22B, all that is required is to remove the used cover from the suction tube 22A by pulling it in the distal direction and then replacing the used (soiled) cover with a fresh cover on the suction tube.

Turning now to FIG. 17 there is shown another and more preferred exemplary system 10' for automatically removing urine from a female patient making use of a more preferred integrated unit 120 having an external female catheter 122 and suction regulator 24' constructed in accordance with this invention and which can be used in a method of this invention.

The system 10' is identical to the system 10 except for the construction of the integrated unit 120, and in particular the suction regulator 24' and the external female catheter 122. The components of the system 10' which are common to the system 10 will be given the same reference numbers and the details of their construction, arrangement and operation will not be reiterated in the interest of brevity. The suction regulator 24' is identical in construction to the suction regulator 24 except that the regulated suction port 24B terminates in a tubular connector 24B'. The tubular connector 24B' is best seen in FIGS. 17 and 18 and is configured to receive the proximal end of a tubing section of the external female catheter 122 so that the regulated suction produced by the suction regulator is applied to the external female catheter. The external female catheter 122 is best seen in FIGS. 17 and 19 and basically comprises an elongated suction tube 122A and a removable liquid permeable cover 122B. The elongated suction tube 122A is best seen in FIGS. 19 and 20 and basically comprises an assembly of an elongated flexible conduit or tubing section 124, an optional cover tube 126, a multi-slot end-piece 128, and a section of malleable wire 130.

The conduit or tube 124 is a section of conventional tubing formed of any suitable flexible material, e.g., flexible PVC tubing, like used in hospitals to carry fluids via suction and has a distal end 124A and a proximal end 124B. The proximal end 124B of the tubing section 124 receives the tubular connector 24B' of the suction regulator 24' to thereby connect the elongated suction tube 122A to the suction regulator. The distal end 124A of the tubing section 124 receives the proximal end 128A of the multi-slot end-piece 128.

The removable liquid permeable cover 122B is in the form of a cylindrical sponge-like body having a rounded or domed distal end. The cover 122B will be described in detail later. Suffice it for now to state that that in one exemplary preferred embodiment of this invention the cover 122B is approximately 5.75 inches long measured from its distal end to its proximal end and has an outside diameter of approximately 1.125 inches. The cover is mounted on the distal end portion of the elongated suction tube 122A and overlies approximately the distal-most 5 inches of the elongated suction tube. In particular, the cover is mounted on and over the distal end 124A of the tubing section 124 and on and over the cover tube 126 and the multi-slot end-piece 128, with the proximal portion of the cover overlying approximately 0.5 inch of the tubing section 124 to ensure an air-tight seal.

The multi-slot end-piece 128 forms a first section of the elongated suction tube and is a flexible rod-like member, e.g., an extrusion of any suitable flexible material, e.g., polyurethane. In the exemplary embodiment shown the end-piece is approximately 5 inches long with an outside diameter of approximately 0.425 inch. The end-piece 128 has a generally circular profile in cross-section (see FIG. 21) and includes plural longitudinally extending passageways or channels 132A, 132B, 132C and 132D, which run the full length to the end-piece. The passageways are equidistantly spaced about the periphery of the end-piece and each passageway includes a narrow width, e.g., 0.1 inch, longitudinally extending slot at the surface of the periphery of the end-piece. In particular, the passageway 132A includes an associated slot 134A, the passageway 132B includes an associated slot 134B, the passageway 132C includes an associated slot 134C, and the passageway 132D includes an associated slot 134D. The proximal end of each of the passageways 134A-134D is open, as is the distal end of each of those passageways. A short length, e.g., 0.5 inch, of the proximal end of the end-piece 124 is disposed within the distal end 124A of the tubing section 124. The tubing section 124 from the proximal end of the end-piece to the connector 24B' of the suction regulator 24' forms what can be called a second section of the suction tube 122A.

The optional cover tube 126 is a section of heat shrinkable tubing, which is disposed over the portion of the end-piece 128 immediately adjacent the distal end 124A of the tubing section 124, thereby covering or closing off the underlying proximal portions of the slots 134A-134D, but leaving approximately 40 mm of the distal end portions of the slots uncovered or exposed. Thus, when the proximal end of the end-piece 128 is disposed within the distal end 124A of the tubing section 124 and the heat shrinkable cover tube 126 is in place, the regulated suction applied from the suction regulator to the tubing section 124 will be applied to the open proximal end of each of the passageways 132A-132D down the length of the passageways to exit the uncovered portions of the slots 134A-134D, respectively, and the open distal ends of those passageways.

It should be noted that while the exemplary embodiment shown and described above includes four passageways and four associated slots, it is contemplated that the end-piece can have any number of passageways, with associated slots, e.g., three passageways and three associated slots. The key feature being that the slots are directed in different, equidistantly spaced radial directions with respect to the central longitudinal axis of the end piece. As such irrespective of the orientation of the elongated external catheter about its central longitudinal axis with respect to the urethra opening of the patient, there will be at least one slot generally directed to the urethra opening to accept urine therefrom. Moreover, the distal end of each of the passageways 134A-134D is open. Thus, when the external female catheter is disposed adjacent the urethra of the patient, and regulated suction applied to it from the suction regulator, the regulated suction is applied to the distal end portion of the cover 122B, i.e., the distal portions of the slots 134A-134D that are not covered by the cover tube 126. That action draws urine from the patient through the distal portion of the cover 122B into the exposed portions of the slots 134A-134D and the open distal ends of the passageways 132A-132D and from there through those passageways into the tubing section 124 and from there through the suction regulator 24' to the collection canister 12. The use of multiple channels facilitates the removal of urine while minimizing the chance that the channels will be collapsed by portions of the patient's anatomy.

As best seen in FIGS. 18 and 21 the end-piece 128 includes a small diameter, e.g., 0.051 inch, central passageway 136 in which the malleable wire 130 is located. The malleable wire can be formed of any suitable material, e.g., stainless steel, aluminum, provided that it is biocompatible and can be readily bent into a desired shape and will hold that shape. With the wire 130 located in the passageway 136 and the cover 122B mounted on the distal portion of the elongated suction tube 122A, the end-piece 128 can be bent into a somewhat arcuate shape, so that the cover 122B conforms closely and comfortably to the anatomy of the patient contiguous with the patient's urethra opening. Other dimensions of the end-piece 128 are shown in FIG. 21.

Turning now to FIG. 19, the details of the cover 122B will now be described. In particular, as mentioned earlier the cover 122B is a cylindrical member whose distal end or tip is rounded or domed and is approximately 5.75 inch in length, and with a 1.125 inch outside diameter. The cover includes a central passageway 138 extending from its proximal end to a point closely adjacent its distal end. The inside diameter of the passageway 138 is approximately 0.375 inch. The thickness of the rounded tip is approximately 0.375 inch. The passageway 138 is configured for receipt of the end-piece 128, the optional cover tube 126, and the distal end portion of the tubing section 124. To that end the internal diameter of the central passageway of the cover 122B is slightly smaller than the external diameter of the end-piece 128 so that the cover 122B is held thereon by friction. With the cover in place, the closed distal end of the cover overlies the open distal ends of the passageways 134A-134D of the end-piece 128.

The cover is formed of a liquid-permeable material, e.g., hydrophilic polyurethane foam, although it could be formed of other liquid permeable hydrophilic materials such as PVA (polyvinyl alcohol) sponge, cellulose, etc. One preferred exemplary embodiment of a hydrophilic polyurethane foam cover is a hybrid foam having a pore size of approximately 150-300 microns, and a density in the range of 16-21 grams.

In accordance with one preferred aspect of this invention the sponge material making up the cover 122B works better if it is pre-moistened with water. Thus, commercial embodiments of this invention will be preferably packaged wet. Since it is packaged wet, the cover preferably will include an antimicrobial additive to prevent microbial growth. Any suitable commercially available anti-microbial additive can be used, e.g., isothiazolinone treatments, zinc pyrithione, thiabendazole, silver and quaternary ammonium compounds and Polyhexamethylene biguanide (PHMB) and chlorhexidine gluconate (CHG). In addition to helping with storage, the antimicrobial agent inhibits the growth of microbes during use of the system of this invention, reducing the risk of infection.

Operation of the external female catheter 120 is similar to the operation of the external female catheter 20 and is as follows. In particular, the suction regulator 24' operates in an identical manner as the suction regulator 24. Thus, when regulated suction produced by the suction regulator 24' is applied connector 24B' of the port 24B that regulated suction will be applied to the exposed distal portions of the slots 134A-134D and the contiguous open distal ends of the passageways 132A-132D, respectively, to draw any urine that the female patient voided into the cover from there into those passageways, whereupon that urine will be pulled into the interior of the tubing section 124 and carried by air from the suction regulator 24'. From there the urine is carried to the receptacle or canister 12. In particular, with the system 10' as described above when suction is applied from the hospital's suction line or wall regulator 16, that high level of suction is conveyed through the tubing section 14, from whence it is applied to the canister or receptacle 12 and the associated tubing section 18 to the line suction port 24A of the suction regulator 24, whereupon it is regulated (e.g., reduced) by operation of the suction regulator to a much lower operating level, e.g., 40 mmHg. That reduced or regulated suction will appear on the suction port 24B of the regulator 24' and from there to the external catheter 122 to thereby draw urine from the external catheter 122 back through the regulator 24', and out through the tubing section 18 into the receptacle or canister 12 for collection therein.

One of the key features of the integral suction regulator and female catheter 120 allows, like the features of the integral suction regulator and female catheter 20, is that it can be used in a system like 10' to be attached to line suction.

This configuration allows for far greater airflow than conventional methods, which aids in urine capture and drying of the catheter. Moreover, the openings through which the regulated suction is applied to the cover 120B is somewhat confined in that only approximately 40 mm of the slots 134A-134D are exposed to provide suction to the contiguous portions of the cover 122B. By decreasing the opening size of the extrusion, i.e., the exposed slots, the subject invention is able to concentrate the same amount of airflow, increasing the velocity of the air to compound the benefits of the high volume of airflow provided by the regulator. However, since the foam component is absorbent regardless of location, over-concentration of the airflow results in location-dependent capture and non-uniform drying and may leave the patient wet or result in leaks. Iterative bench-top testing has suggested providing open slots of approximately 40 mm/1.5 inch results in optimal performance, as defined by the maximum capturable urination rate before the system is overwhelmed and leaks.

As should be appreciated by those skilled in the art, when the tubing in an external catheter circuit becomes filled with urine, either due to a patient urinating a large volume at once, or a temporary occlusion along the circuit, air entrainment is no longer possible, and urine must be pulled through the tubing by the force of suction alone. In this scenario, for any section of tubing traveling along a vertical incline, gravity opposes the suction force limiting the height of any vertical incline which can be overcome. 40 mmHg is equivalent to the pressure exerted by approximately 21 inches of water, meaning that for any suction-based urine management system operating at 40 mm Hg no part of the system can have a vertical incline greater than 21 inches without risking failure if the external catheter circuit becomes filled with urine. Conventional external catheter systems, (which may have a tubing path of up to 20 feet between the wall regulator and the patient) present a significant possibility that some portion of the tubing path may have a 21 inch incline, so that such prior art systems are prone to that type of failure if the external catheter circuit becomes filled with urine. In contradistinction, the systems of this invention make use of tubing that is only approximately 6 inches to approximately 24 inches between the regulator and patient's urethra opening. This means that the integrated suction regulators/external catheters of the subject invention should not be prone to failure due to too much urine.

It must be pointed out at this juncture that the various components of the integrated unit 20 and 120 shown and described above are merely exemplary of various components that may be used in accordance with this invention to provide the capabilities as discussed above. Thus, various changes can be made to the integrated external female catheter and suction regulator of subject invention from the exemplary embodiments described above. For example, the use of the optional cover tube 126 can be omitted. In such a case the distal end 124A of the tubing section 124 should extend to approximately 40 mm from the distal end of the end-piece 128, whereupon the tubing section 124 itself closes off the slots in the passageways up to the last (distal) 40 mm of the end-piece. The use of the optional heat shrinkable tube section 126 is a preferred means for covering portions of the slots proximally of the distal-most 40 mm thereof, since heat shrinkable tubing is more economical than the material making up the tubing section 124. Moreover, the end-piece 124, itself, can be constructed so that the slots 134A-134D do not extend the entire length of the associated passageways 132A-132D, but only the distal-most 40 mm thereof. Thus, it is contemplated that the end-piece can be constructed so that only the distal-most portion, e.g., approximately 40 mm, of the passageways 132-132D include slots 134A-134D, so long as the remaining portion of the passageways are configured to carry suction therethrough without leakage and so long as the entire length of the end-piece along which the cover 122B extends is malleable to be conformable to the anatomy of the patient.

Moreover, the suction regulators 24 and 24' may be constructed somewhat similarly to the suction controller 300 shown in FIGS. 9A and 10A of U.S. application Ser. No. 14/227,587 entitled the Gastric Sizing Systems Including Instruments And Methods Of Bariatric Surgery filed on filed on Mar. 27, 2014, now U.S. Pat. No. 10,646,625, which is assigned to the same assignee as this invention and whose disclosure is specifically incorporated by reference herein. That suction controller if used in an integrated unit 20 or 120 like the subject invention would be modified to omit the disk 314 and thus result in a cost saving. In the invention of that patent the disk 314 is provided to seal off the system when positive pressure is applied for leak testing. The integrated unit 20 of this invention and any other integrated units constructed in accordance with this invention will never exceed atmospheric pressure, so a disk 314 is unnecessary. Moreover, the suction controller 300 of that patent if used in an integrated unit like that of this invention will need to be sized and configured to produce the desired regulated suction value, e.g., 40 mmHg.

Various other changes can be made to systems of this invention, in addition to changes in the suction regulator 24 and 24'. For example, some hospitals in which the subject integrated unit will be used have special regulator set-ups that allow for connection of a suction canister directly below the wall regulator. In such a case the tubing section 14 of the system 10 may be omitted. Also, it should be pointed out that the integrated units of this invention are not limited to use in hospitals, but can be used in any application providing care to a patient.

Without further elaboration the foregoing will so fully illustrate our invention that others may, by applying current or future knowledge, adopt the same for use under various conditions of service.

We claim:

1. An external catheter configured to be coupled to a source of suction and a receptacle or canister for automatically removing by suction urine voided by a female and providing that urine to the receptacle or canister, said external catheter being configured for external disposition in fluid communication with a urethra opening of the female, whereupon urine voided by the female is received by said external catheter, said external catheter comprising:

an elongated suction tube having a longitudinal central axis and comprising a first section and a second section, said second section being configured to be coupled to the source of suction and to the receptacle or canister, said first section having a distal end, a proximal end, at least one first passageway extending longitudinally through said first section from said distal end to said proximal end, slot extending longitudinally along said at least one first passageway from said distal end to a point adjacent a middle of said first section whereupon said at least one slot is confined to a distal end portion of said first section, such that a length of said continuous elongated slot is between said distal end and said point adjacent of said middle of said first section, said at least one continuous elongated slot being in fluid communication with said at least one first passageway, said second section being located proximally of said first section and comprising a second passageway configured to be coupled to the source of suction and to the receptacle or canister and in fluid communication with said at least one first passageway, and a one-piece cover formed of a liquid permeable material having a longitudinal central axis and an external surface, said external surface including a distal external end surface portion, and an arcuate external surface portion, said arcuate external surface portion being arcuate along a length thereof and extending around said longitudinal central axis from said distal external end surface portion to a proximal end of said arcuate external surface portion, said cover being directly disposed over and about said elongated suction tube to completely cover said first section whereupon said distal end of said elongated tube section is located within said cover adjacent said distal external end portion and in direct engagement with said cover whereupon a portion of said cover overlies said at least one slot so that said at least one slot is available to directly receive urine through said portion of said cover and with all of said arcuate external surface exposed so that any portion of said arcuate external surface portion is brought into engagement with a portion of the female adjacent the urethral opening, whereupon when said external catheter is coupled to the source of suction, suction is applied down said second passageway into said at least one first passageway and through said at least one slot to draw urine through said cover into said at least one slot, and through said at least one first passageway and said second passageway to said receptacle or canister.

2. The external catheter of claim 1, wherein said distal end of said first section is open.

3. The external catheter of claim 1, wherein said first section is malleable.

4. The external catheter of claim 3, wherein said cover comprises a sponge material.

5. The external catheter of claim 1, wherein said first section comprises at least three equidistantly spaced longitudinal passageways and at least three continuous elongated slots extending along said at least three equidistantly spaced longitudinal passageways.

6. The external catheter of claim 5, wherein said first section includes a central passageway surrounded by said at least three equidistantly spaced longitudinal passageways and a malleable wire extending through said central passageway.

7. The external catheter of claim 5, wherein said cover comprises a sponge material.

8. The external catheter of claim 1, wherein said cover comprises a sponge material.

9. The external catheter of claim 1 wherein said cover is 5 inches long and wherein said at least one elongated slot is 40 mm long.

10. The external catheter of claim 1, wherein said first section comprises at least three equidistantly spaced longitudinal passageways and at least three continuous elongated slots extending along said at least three equidistantly spaced longitudinal passageways.

11. The external catheter of claim 10, wherein said first section includes a central passageway surrounded by said at least three equidistantly spaced longitudinal passageways and a malleable wire extending through said central passageway.

12. The external catheter of claim 1, wherein said cover is removable.

13. The external catheter of claim 12, wherein said removable cover comprises a sponge material.

14. The external catheter of claim 1, wherein said external catheter is a component of an integrated unit, said integrated unit comprising the receptacle or canister and a suction regulator.

15. The integrated unit of claim 14, wherein said receptacle or canister comprises a first port, a second port, and a hollow interior in fluid communication with the first and second ports, said first port being configured to be connected to the source of suction, and wherein said suction regulator comprises:

a first port in fluid communication with said proximal end of said elongated suction tube to provide suction at a regulated value thereat to carry urine from said external catheter through said suction regulator and through said suction port into the second port of the receptacle or canister for collection in the hollow interior of the receptacle or canister.

16. The integrated unit of claim 15, wherein said regulated value of suction is within the range of 40-60 mmHg.

17. The integrated unit of claim 16, wherein the urine is carried through said suction regulator into said receptacle or canister by air, which is flowing at a flow rate up to 100 standard cubic feet per hour.

18. The integrated unit of claim 15, wherein the urine is carried through said suction regulator into said receptacle or canister by air, which is flowing at a flow rate up to 100 standard cubic feet per hour.

\* \* \* \* \*